United States Patent [19]

Byler

[11] 4,249,803
[45] Feb. 10, 1981

[54] OPTICAL DEVICE FOR PRE-OPERATIVE CATARACT PATIENTS

[75] Inventor: William H. Byler, 804 Village La., Winter Park, Fla. 32792

[73] Assignees: William H. Byler; Thelma T. Byler, both of Sarasota, Fla. ; Trustees of William H. Byler Revocable Trust

[21] Appl. No.: 56,269

[22] Filed: Jul. 10, 1979

[51] Int. Cl.³ .............................................. G02C 7/16
[52] U.S. Cl. ........................................ 351/46; 351/47
[58] Field of Search ...................... 351/46, 47, 41–45; 2/14; 46/1

[56] References Cited

U.S. PATENT DOCUMENTS

| | | | |
|---|---|---|---|
| 1,907,356 | 5/1933 | Klein | 351/44 |
| 3,967,885 | 7/1976 | Byler | 351/46 |
| 4,012,129 | 3/1977 | Byler | 351/46 |

Primary Examiner—John K. Corbin
Assistant Examiner—B. Wm. de los Reyes
Attorney, Agent, or Firm—Pennie & Edmonds

[57] ABSTRACT

An improved optical device in combination with means for holding the device in position before the eye including an optical device formed of an opaque mask for mounting before the eye, a horizontal transparent area extending substantially across the mask centrally thereof, an array of discrete circular transparent areas on the mask, the array being disposed below the horizontal transparent area and each circular area having equal diameters of between 0.5 and 1.2 mm. is characterized by an increase in the total aperture of the transparent areas on those portions of the opaque mask where the eye-to-mask distance increases thereby permitting a greater field of vision while limiting the influx of light.

9 Claims, 4 Drawing Figures

OPTICAL DEVICE FOR PRE-OPERATIVE CATARACT PATIENTS

TECHNICAL FIELD

The present invention relates to an improved optical device especially constructed for pre-operative cataract patients. The improved optical device is characterized by a specially constructed opaque mask attached to means for mounting before the eyes, such as spectacle frames or the like, which results in improved side vision without significant increase of total exposure of the eyes to light.

BACKGROUND ART

Patients inflicted with cataracts in one or both eyes must sometimes undergo corrective treatment to remove the cataracts. Prior to corrective treatment, the cataract patient finds, typically, that his vision deteriorates over a period of time. Generally, prescription lenses are worn to provide optimum acuity. These lenses, however, do not fully correct the imaging capability of the eye.

Cataracts have a light-scattering effect so that the light entering the eye through a wide angle is spread over the retina. The light-scattering effect resulting from the cataract reduces the contrast of images viewed, thus making such images appear blurred. This is a particularly serious problem in higher ambient light conditions, such as on beaches and on bright, sunshiny days. Also, at night, headlights of cars flood the eyes with light. Normal eyes, when directed to the road, are only minimally affected. However, the light from the headlights of cars is scattered by cataracts and presents a problem to cataract patients wishing to drive at night.

In my earlier patent, Byler U.S. Pat. No. 4,012,129, there is disclosed an optical device for pre-operative cataract patients comprising an opaque mask attached to spectacle frames or other means for mounting before the eyes. The mask includes a horizontally extending slotted transparent area or opening through which the patient's vision is unobstructed. The mask further includes an array of transparent areas or openings disposed below the slotted opening. The size and positioning of the areas or openings of the array are interrelated with the slotted opening to provide an increased vertical field of vision while restricting the light striking the patient's eye to a minimum.

Under certain conditions, an opaque mask such as related by the Byler '129 patent may restrict the user's clear field of vision. Specifically, a narrow horizontal area can restrict the user's clear field of vision through the side portions of the mask. The restriction of the side vision is an especially important consideration when the user is in a mobile situation, such as driving, which requires constant adjustment.

DISCLOSURE OF INVENTION

According to the present invention, an improved optical device is in combination with means for holding the device in position before the eye. The optical device includes an opaque mask for mounting before the eye, a horizontal transparent area which extends across the mask centrally thereof throughout a distance at least as far as useful side vision extends, and an array of discrete circular transparent areas on the mask, the array being disposed below the horizontal transparent area and each circular area having equal diameters of between 0.5 and 1.2 mm. The improved device is characterized by an increase in the total aperture of the transparent areas on those portions of the opaque mask where the eye-to-mask distance increases substantially, thereby permitting a clearer field of vision while limiting the influx of light.

It has been found that by widening the horizontal transparent area primarily or only in the side portion of the mask where the eye-to-mask distance increases substantially, one avoids the restricted side vision of the prior art, which may occur when the user looks sharply to the side or rear. In this situation, due to the need for precisely correct tilt of the head, viewing is liable to be through the less transparent aperture array rather than through the horizontal transparent area. Higher ambient light conditions require narrower horizontal transparent areas. As the horizontal area decreases in height, the user must increase the vertical head movement so as to compensate for the restricted side vision.

The increase in the side vision in the present invention is accomplished while maintaining major limitation of the total amount of light reaching the eye. To this end, as discussed generally, widening of the horizontal transparent area may begin at an angular location of about 60° from a straight-ahead line of sight. This widening of the horizontal transparent area adds relatively little to the total effective light when viewing through the central region in substantially a straight-ahead line of sight by virtue of the fact that the light enters the eye at such a large angle.

The array of discrete circular transparent areas pertains to clarity of vision, and it is a principal function of the array to extend the field of vision with only a minimum increase of total effective light admitted to the eye. The circular transparent areas of the array preferably are both sized and spaced to permit complete imaging of the field of vision while, at the same time, one may only have a minimal awareness of pattern. Importantly, it has been found, there is a need to maintain effective transparency within the lower region of the array at greater angular spacing from the straight-ahead line of sight. To this end, the circular transparent areas in vertical columns may be closer together or they may be of a diameter larger than the diameter of transparent areas in the vertical columns closer to the straight-ahead line of sight. The need to similarly locate the transparent areas in horizontal columns for the purpose discussed is largely obviated by the curvature of the mask (see FIGS. 1 and 3) which tends to minimize the foreshortening effect in the lower region and because a large proportion of viewing is through the central region. If the mask is generally planar (see FIGS. 2 and 4), the considerations set out above with regard to vertical spacing may be resorted to in horizontal columns as the angular spacing from the straight-ahead line of sight increases.

Regarding the utilization of the present invention, the opaque mask may be mounted within normal spectacle frames. The mask may also be mounted directly on prescription glasses. Alternatively, the mask may be made as a separate unit to be attached to the spectacle frame over the patient's prescription lenses, as with ordinary clip-on sunglasses. Two masks formed as an integral structure would facilitate spectacle frame mounting.

Still another frame type unit is made from suitable sheet plastic shaped to hang on spectacle frames from the back side and curved to form side pieces which provide extra protection against side-entering light. The improved film attaches easily to the above surfaces.

The present invention provides an improved optical device in the form of an opaque mask wherein the user derives increased clarity of the field of vision allowing greater mobility. Furthermore, the increased clarity is accomplished while maintaining a low level of light exposure to the pre-operative cataract patient's eye thereby permitting good imaging.

BRIEF DESCRIPTION OF THE DRAWINGS

A preferred way of carrying out the invention is described in detail below with reference to drawings which illustrate specific embodiments, in which.

BEST MODE FOR CARRYING OUT THE INVENTION

Figure 1:
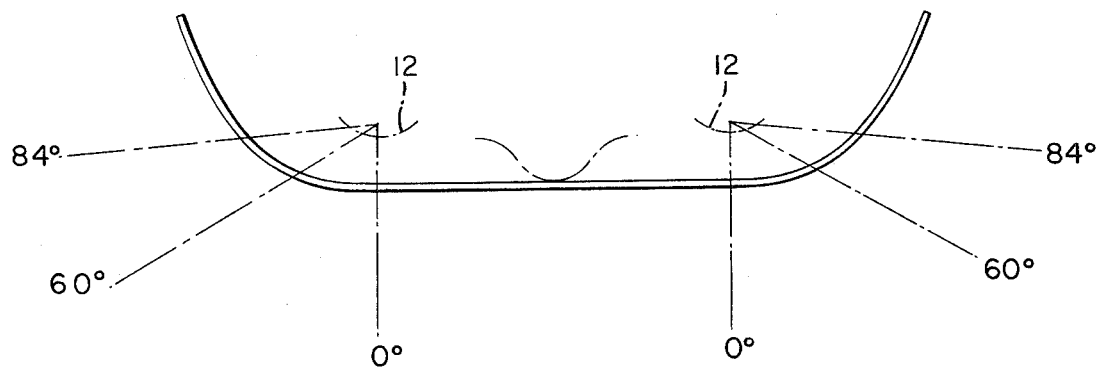
FIG. 1 is a plan view of the optical mask of the present invention showing the degree of lateral vision therethrough.
Figure 3:
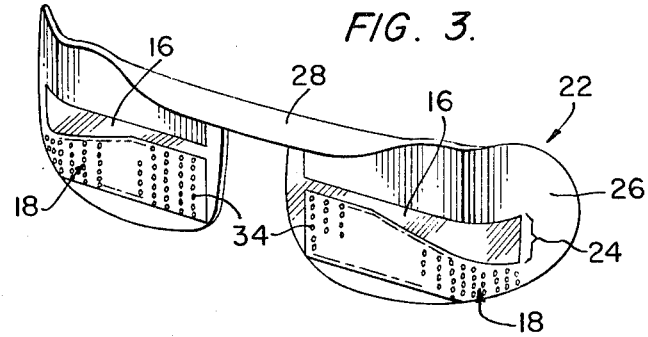
FIG. 3 is a perspective view of the optical mask as seen generally in FIG. 1; and, FIG. 4 is a front view of a pair of eyeglasses frames incorporating two of the optical masks of the present invention.

FIG. 1 is a plan view of an optical mask, see also FIG. 3 wherein the mask is illustrated in perspective view, before the eyes 12 and includes pairs of dot-dash lines representing the approximate maximum range for macular vision with the head still, about 84° from a straight-ahead line of sight or centerline of 0°, and a pair of dot-dash lines representing the approximate range of normal vision with eyes still (about 60°). Peripheral vision may extend beyond 90°. It can be readily seen that the eye-to-mask distance increases toward the angle of peripheral vision. In fact, the eye-to-mask distance more than doubles at the 84° lateral vision point. The maintenance of a constant horizontal transparent area height with an increase in the distance between the eye and the transparent area results in a decrease in the vertical field of vision. Thus, as the eye moves laterally, the vertical field of vision tends to be reduced. It is an important aspect of the present invention to incorporate a flare 24 in the horizontal transparent area which tends to increase the side field of vision. The flare commences from the lower or bottom edge of the horizontal transparent area and slopes downwardly toward the side portions of the mask. The upper edge of the transparent area is horizontal throughout its length. This configuration of the transparent area is preferred primarily because it minimizes aperture pattern as seen by the eye. However, the basic purposes may be served, also, by other configurations having an aperture pattern which widens stepwise or which may be described by curved edges. Additionally, both the upper and lower edges of the aperture may be flared.

Figure 2:
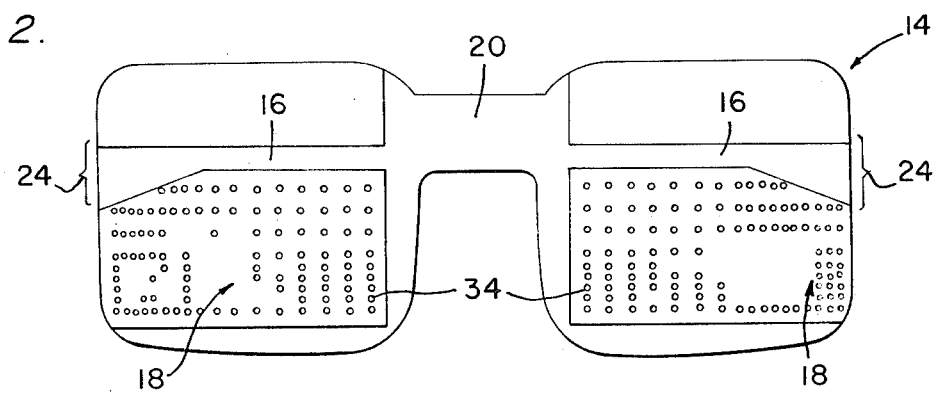
FIG. 2 is a front view of another form of the optical mask of the present invention.

The optical mask 14 of FIG. 2 is preferably formed of thin, opaque material, such as photographic film or opaque plastic with the horizontal transparent area 16 and the array 18 of discrete circular transparent areas produced photographically or by other suitable means located thereunder. The horizontally disposed area has a lower portion which diverges at about 60° from the centerline downwardly to provide increased opening for light from the side. The depth of the divergence can be more than double the height at the other end. The depth may be up to about 10 mm. In order to maintain the alignment of the two horizontal areas in a level position when attached to the eyeglass frame, the two masks are integrally connected by a bridging portion 20 which generally will align with the bridging portion of a conventional eyeglass frame.

In addition to the integral, formed masks of FIG. 2, a pair of masks may be provided on a conventional clip-on type frame. Frames of the clip-on construction type are readily available. The clip-on type of construction would be provided with bendable clips, not shown, for attaching to conventional eyeglass frames.

The preferred embodiment of the present invention is shown in FIG. 3. In the Figure, a pair of optical devices 22 having a wrap-around configuration are provided. As with the form of the invention in FIG. 2, a horizontal transparent area 16 is provided at eye level with an array 18 of discrete circular transparent areas thereunder. The wrap-around configuration extends the mask protection laterally beyond the eyes. Side sections 26 extend laterally and backward of the individual's eyes to the area of the temples. These sections provide physical protection beyond the operative areas of the masks. Since, in the wrap-around configuration, the side section of the optical devices extend beyond the range of peripheral vision (on the order of 15 mm beyond), it may be desirable to terminate the transparent areas at about that distance from the end of each section.

A top section 28 which is curved forwardly and downwardly connect the optical devices. The top section provides a means for hanging the device on conventional eyeglass frames.

Figure 4:
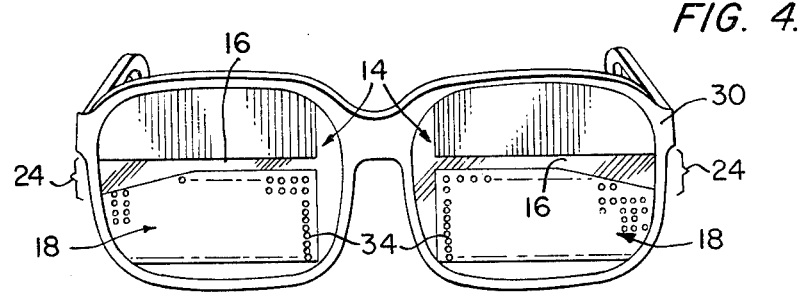

In FIG. 4, a pair of eyeglass frames 30 is shown which incorporates the optical device 14 of the present invention, one device being provided for each eye. Each optical device is fabricated from an opaque material, such as photographic film or sheet material, which can be cut into a plate mask 32 for fitting into the eyeglass frames or bonded to the lenses.

A horizontally extending transparent area 16 is disposed on each opaque mask. The area is located at eye level when the mask is positioned before the eye. An array 18 of discrete circular transparent areas 34 is located below the horizontal area. Where the mask is constructed from photographic film, both the horizontal area 16 and the discrete circular areas 34 may be transparently formed. Alternatively, openings can be cut completely through the mask. As shown, the areas 34 are circular in shape.

In accordance with the teachings of the present invention, the spacing and overall pattern and relationship of the circular transparent areas with that of the horizontal transparent area is important. Specifically, the height of the slot in the central portion of the mask is between about 1 mm. and about 6 mm. and may widen to as much as 10 mm. at the outer end. As to the discrete circular areas, they have equal diameters of between about 0.5 and 1.2 mm. and may be spaced equally from each other in the horizontal direction on centers of from about 1.5 to 4 mm. Spacing within the same range will prevail in the vertical direction. However, there is a major advantage in spacing lower rows more closely than upper rows. Thus, due to the foreshortening effect of apertures on light passing through at an angle and the fact that the angle is greatest through the lower apertures, spacing within the lower rows is reduced as a means toward maintaining the level of effective transmission of light at the locations at which eye-to-mask distance is greatest, the spacing is least to tend to maintain transmission of light. The array provides a major extension of the vertical range of vision while adding a minimal increment to overall transmission. Overall transparency of useful slot-array combinations may be less than 5% while allowing relatively clear vision through the slot portion; or, by tinting any or all of the openings or using such combinations in combination with ordinary sunglasses, overall transmission can be as low as 1% while allowing good mobility in high ambient light conditions, such as at the beach, etc. Even if sunglasses of such low transmission were available, they would have little, if any, usefulness because they would not allow the user the option of vision through a transparent area which has significantly higher transmission than the overall device.

Having described the invention with particular reference to the preferred form thereof, it will be obvious to those skilled in the art to which the invention pertains after understanding the invention, that various changes and modifications may be made therein without departing from the spirit and scope of the invention as defined by the claims appended hereto.

I claim:

1. An improved optical device in combination with means for holding the device in position before the eye, said optical device including an opaque mask for mounting before the eye, a horizontal transparent area extending substantially across the mask at eye level, an array of discrete circular transparent areas on the mask, the array being disposed below the horizontal transparent area and each circular area having equal diameters of between 0.5 and 1.2 mm. is characterized by an increase in the total aperture of the transparent areas on those portions of the opaque mask where both the eye-to-mask distance and angular spacing from a straight-ahead line of sight increases substantially thereby permitting a clearer field of vision and improved clarity while limiting the influx of light.

2. An improved optical device as recited in claim 1 wherein the increase in transparent areas as the eye-to-mask distance increases is characterized by the horizontal transparent area:
   (a) having a height between about 1 mm. and about 6 mm. in the central portion of the mask; and
   (b) a substantially greater height at the sides of the mask.

3. An improved optical device as recited in claim 2 wherein the greater height at the sides of the mask is characterized by:
   (a) the upper edge of the horizontal transparent areas being horizontal; and
   (b) the lower edge of the horizontal transparent area being:
      (i) horizontal in the central mask portion, and
      (ii) downwardly sloping at the side mask portion.

4. An improved optical device as recited in claim 1 wherein the increase in transparent areas as the eye-to-mask distance increases is characterized by the array of discrete circular transparent areas having a decreasing spacing between individual circular transparent areas in both the outwardly horizontal and downwardly vertical directions.

5. An optical device in combination with means for holding the device in position before the eye, said optical device including:
   (a) an opaque mask for mounting before the eye;
   (b) a horizontal transparent area extending across said opaque mask at eye level, said horizontal transparent area having a height of about 1 to about 6 mm. within a central portion and widened toward the side end to a height of no more than about 10 mm.;
   (c) an array of discrete circular transparent areas on said mask, said circular transparent areas being disposed below said horizontal transparent area and each having equal diameters of between about 0.5 and 1.2 mm. and located on centers spaced equally from each other from between about 1.5 to 4 mm.; and
   (d) said mask being opaque above the slotted opening.

6. An improved optical device as recited in claim 5 wherein the greater height at the side end of the opaque mask is characterized by:
   (a) the upper edge of said horizontal transparent area being horizontal; and
   (b) the lower edge of said horizontal transparent area being:
      (i) horizontal in said central portion, and
      (ii) downwardly sloping toward said side end.

7. The improved optical device of claim 1 or 5 wherein said array is arranged in parallelogram pattern with horizontal spacing equal in the range of from 1.5 to 4 mm. centers and the vertical center to center spacing of the bottom rows being less than that of the upper rows, all within the 1.5 to 4 mm. range.

8. The improved optical device as recited in claim 1 or 5 wherein one or more of said transparent areas are tinted to reduce transmission of light therethrough.

9. The improved optical device as recited in claim 1 or 5 wherein the shape of said opaque mask is such to extend at the sides to the area of the temples, and each said horizontal transparent area terminates at about 15 mm. from the mask end.

* * * * *

UNITED STATES PATENT AND TRADEMARK OFFICE
CERTIFICATE OF CORRECTION

PATENT NO. : 4,249,803
DATED : February 10, 1981
INVENTOR(S) : William H. Byler

It is certified that error appears in the above-identified patent and that said Letters Patent are hereby corrected as shown below:

In the masthead of the patent, correct the address of the inventor to read:

5017 Vivienda Way
Sarasota, Florida 33580

Signed and Sealed this

Twenty-third Day of June 1981

[SEAL]

Attest:

RENE D. TEGTMEYER

Attesting Officer

Acting Commissioner of Patents and Trademarks